US008541624B2

(12) United States Patent
Hagiwara et al.

(10) Patent No.: US 8,541,624 B2
(45) Date of Patent: Sep. 24, 2013

(54) PALLADIUM CATALYST AND PROCESS FOR PRODUCTION OF BISARYL COMPOUND USING SAME

(75) Inventors: Hisahiro Hagiwara, Niigata (JP); Norio Tsubokawa, Niigata (JP)

(73) Assignee: Niigata University, Niigata (JP)

( * ) Notice: Subject to any disclaimer, the term of this patent is extended or adjusted under 35 U.S.C. 154(b) by 0 days.

(21) Appl. No.: 13/510,524

(22) PCT Filed: Nov. 11, 2010

(86) PCT No.: PCT/JP2010/070101
§ 371 (c)(1),
(2), (4) Date: May 17, 2012

(87) PCT Pub. No.: WO2011/062109
PCT Pub. Date: May 26, 2011

(65) Prior Publication Data
US 2012/0232310 A1    Sep. 13, 2012

(30) Foreign Application Priority Data

Nov. 20, 2009 (JP) ................................ 2009-265484

(51) Int. Cl.
C07C 45/68    (2006.01)
C07C 1/26     (2006.01)
C07C 1/32     (2006.01)

(52) U.S. Cl.
USPC ........................... 568/316; 568/640; 585/469

(58) Field of Classification Search
USPC .................................. 568/316, 640; 585/469
See application file for complete search history.

(56) References Cited

FOREIGN PATENT DOCUMENTS
JP    2008184418 A    8/2008
WO    2008118097 A1   10/2008

OTHER PUBLICATIONS

Patent Cooperation Treaty, 'International Search Report' mailed Jan. 22, 2011, ISA Japanese Patent Office; 5 pages.
Hagiwara, H. et al., Nano-silica PAMAM Dendrimer as a Novel Catalyst for Knoevenagel Reactions, Chem. Lett., Sep. 2009, vol. 38, No. 9, p. 926-927, Scheme 1.
Alper, H. et al., Heck reaction using palladium complexed to dendrimers on silica, Can. J.Chem., Jun. 2000, vol. 78, No. 6, p. 920-924, Fig. 1.
Li, Y. et al., The Effect of Stabilizers on the Catalytic Activity and Stability of Pd Colloidal Nanoparticles in the Suzuki Reactions in Aqueous Solution, J. Phys. Chem. B, Sep. 2001, vol. 105, No. 37, p. 8938-8943, 'Experimental Section', 'Preparation of Dendrimer-Pd Nanoparticles'.
Hisahiro Hagiwara et al., "Nano Silica Dendrimer Koteika Pd Shokubai no Kaihatsu to Suzuki-Miyaura Hanno eno Tenkai", 90th Annual Meeting of Chemical Society of Japan in Spring (2010) Koen Yokoshu IV, Mar. 2010, p. 1557, fig. 1.
Kaneda, Kiyoomi, "Green Carbon-carbon Bond-forming Reactions by Heterogeneous Metal Catalysts", J. Synth. Org. Chem. Japan, 61: 436 (2003).
Yamada, "Development of Novel Solid-Phase Polymeric Catalysts for Organic Syntheses", Yakugaku Zasshi 125(10) 749-770 (2005), The Pharmaceutical Society of Japan; Jun. 23, 2005.

*Primary Examiner* — Sikarl Witherspoon
(74) *Attorney, Agent, or Firm* — Duane Morris LLP; J. Rodman Steele, Jr.; Gregory M. Lefkowitz

(57) ABSTRACT

Disclosed are: a novel palladium catalyst which does not undergo leakage, can be recycled, does not require the use of any phosphorus-containing ligand, and has a high catalytic activity; and a process for producing a novel bisaryl compound using the palladium catalyst. In the production of a bisaryl compound by reacting an aromatic halide with an aromatic boronic acid in the presence of a palladium catalyst and a base, the palladium catalyst comprises a dendrimer containing a silica particle as a core and a palladium compound dissolved in an ionic liquid and supported on the dendrimer.

7 Claims, No Drawings

PALLADIUM CATALYST AND PROCESS FOR PRODUCTION OF BISARYL COMPOUND USING SAME

CROSS-REFERENCE TO RELATED APPLICATIONS

This application is a §371 national stage entry of International Application No. PCT/JP2010/070101, filed Nov. 11, 2010, which claims priority to Japanese Patent Application No. JP2009-265484 filed Nov. 20, 2009, the entire contents of which are incorporated herein by reference.

TECHNICAL FIELD

The present invention relates to a palladium catalyst for Suzuki-Miyaura reaction and a method for producing a bisaryl compound using the same.

BACKGROUND ART

Suzuki-Miyaura reaction is a coupling reaction of an aromatic halide and an aromatic boronic acid. This reaction is catalyzed by palladium in the presence of a base, and conventionally needs a phosphorous-containing ligand for activation of the catalyst. Further, because a bisaryl compound of the product is useful for pharmaceuticals and an organic electronic material, the reaction has been utilized not only for a basic research, but also for industries.

However, because palladium is expensive and its contamination to products is regulated, a novel palladium catalyst which does not cause leakage and can be recycled has been sought. Also a catalyst which has a high catalytic activity and does not require a use of an expensive and toxic phosphorous-containing ligand has been demanded.

As for recycling of a palladium catalyst after the use for reaction, non-patent document 1 discloses that a palladium catalyst supported on a hydroxyapatite has an activity for Suzuki-Miyaura coupling reaction between bromobenzene and phenylboric acid, and has a high turnover number (TON). However, the catalyst has also disadvantages such as slightly low catalytic activity and necessity of a severe condition of reaction as high as 120° C.

Additionally, non-patent document 2 discloses a solid-phase palladium catalyst, using a non-cross-linked amphipathic macromolecule with a ligand of arylphosphine, has an activity for Suzuki-Miyaura reaction and also a high TON. However, as is the case with non-patent document 1, the catalyst requires a severe reaction condition as high as 100° C. Furthermore, the catalyst had another disadvantage that the cost for production of the non-cross-linking amphipathic macromolecule is expensive.

Whilst, the inventors developed a palladium catalyst dissolved in an ionic liquid and supported on a porous carrier (patent document 1), however, it is desirable to provide a more excellent palladium catalyst.

PRIOR ART DOCUMENTS

Patent Document

Patent document 1: Japanese unexamined patent application publication No. 2008-184418.

Non-Patent Documents

Non-patent document 1: Kaneda, Kiyoomi, J. Synth. Org. Chem. Japan, 61: 436 (2003)

Non-patent document 2: Yamada, Yoichi, YAKUGAKU ZASSHI, 125: 749 (2005)

DISCLOSURE OF THE INVENTION

Problems to be Solved by the Invention

Therefore, it is an object of the invention to provide a novel palladium catalyst having a high catalytic activity which does not cause leakage, can be recycled, does not require a use of any phosphorus-containing ligand, and a method for producing a novel bisaryl compound using the palladium catalyst.

Means for Solving the Problem

The inventors have diligently studied to solve the above problem, and found that Suzuki-Miyaura reaction proceeds with a high yield by use of the palladium catalyst which comprises a dendrimer containing a silica particle as a core and a palladium acetate supported on the dendrimer with use of an ionic liquid, and thus, conceived the present invention.

Specifically, a method of the present invention for producing a bisaryl compound comprises a use of a palladium catalyst in the production of the bisaryl compound by reacting an aromatic halide with an aromatic boronic acid in the presence of the palladium catalyst and a base, wherein the palladium catalyst comprises a palladium compound dissolved in an ionic liquid and supported on a dendrimer containing a silica particle as a core.

Additionally, the dendrimer containing the silica particle as the core is characteristically represented by the following formula, wherein $R^1$, $R^2$ is selected from hydrogen and methyl group.

[Formula 1]

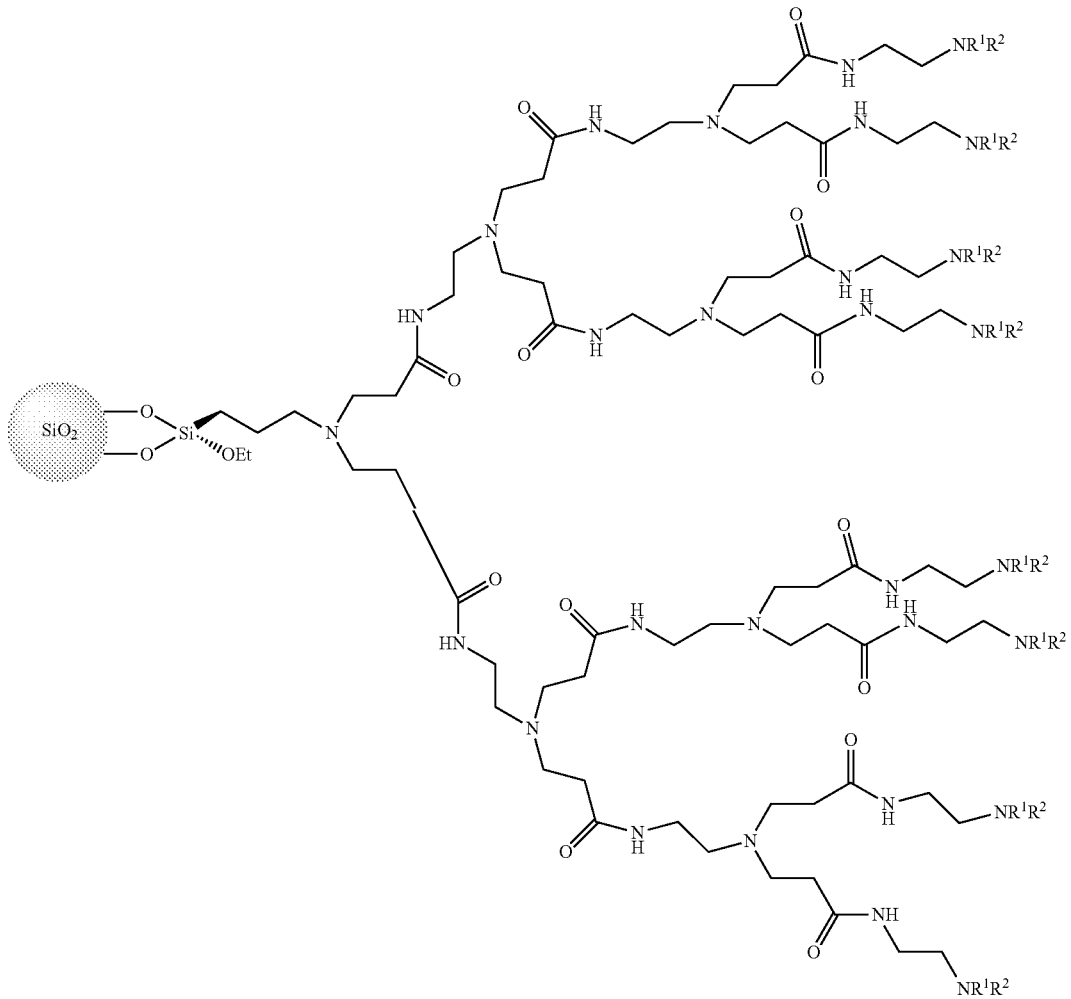

Further, a diameter of the silica particle is characteristically in a range of 1 to 100 nm.

In addition, the palladium compound is characteristically palladium acetate.

Furthermore, the ionic liquid is characteristically 1-butyl-3-methylimidazolium hexafluorophosphate.

Moreover, the ionic liquid is characteristically 1-butyl-3-methylimidazolium bis(trifluoromethane sulfonyl)imide.

Additionally, the ionic liquid is 1-hexyl-3-methylimidazolium hexafluorophosphate.

In addition, the base is characteristically potassium carbonate, and the aromatic halide reacts with the aromatic boronic acid characteristically in a mixture solvent of water and ethanol.

A palladium catalyst of the invention characteristically comprises a palladium compound dissolved in an ionic liquid and supported on a dendrimer containing a silica particle as a core.

Additionally, the dendrimer containing the silica particle as the core is characteristically represented by the following formula, wherein $R^1$, $R^2$ is selected from hydrogen and methyl group.

[Formula 2]

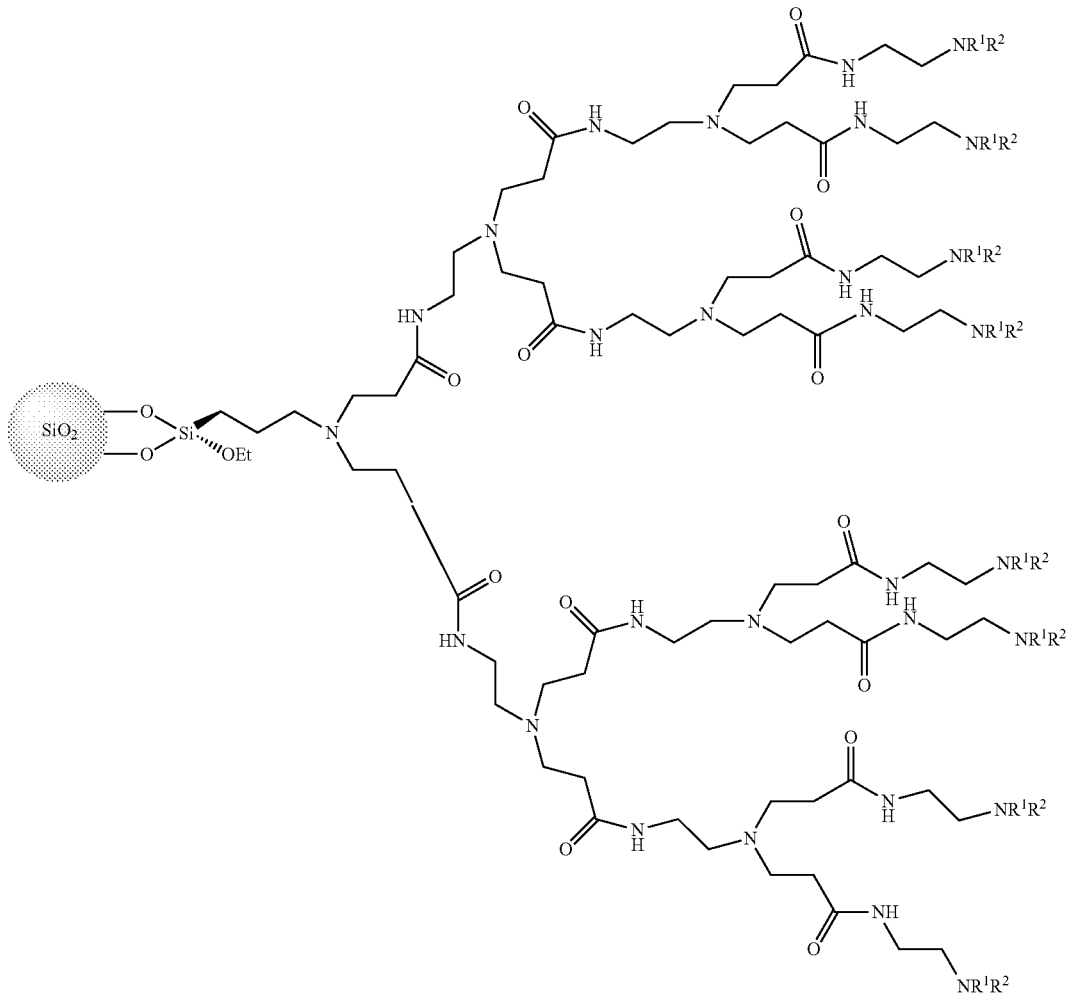

In addition, a diameter of the silica particle is characteristically in a range of 1 to 100 nm.

Further, the palladium compound is characteristically palladium acetate.

In addition, the ionic liquid is characteristically 1-butyl-3-methylimidazolium hexafluorophosphate.

Furthermore, the ionic liquid is characteristically 1-butyl-3-methylimidazolium bis(trifluoromethane sulfonyl)imide.

Moreover, the ionic liquid is characteristically 1-hexyl-3-methylimidazolium hexafluorophosphate.

The Effect of the Invention

The present invention provides a novel palladium catalyst which does not cause leakage, can be recycled, and has a high catalytic activity which does not require use of any phosphorous-containing ligand; and, a method for producing a novel bisaryl compound using the palladium catalyst.

THE EMBODIMENT OF THE INVENTION

The palladium catalyst of the invention comprises a palladium compound dissolved in an ionic liquid supported on a dendrimer containing a silica particle as a core.

In the present invention, for the dendrimer containing the silica particle as the core, any dendrimer can be used without any limitation on its type or its number of branches, provided that the palladium compound dissolved in the ionic liquid can be supported on the dendrimer. As an example, a dendrimer represented by the following formula can be used, wherein $R^1$, $R^2$ is selected from hydrogen and methyl group. Whilst, a range of 1 to 100 nm of the silica particle diameter is preferably used.

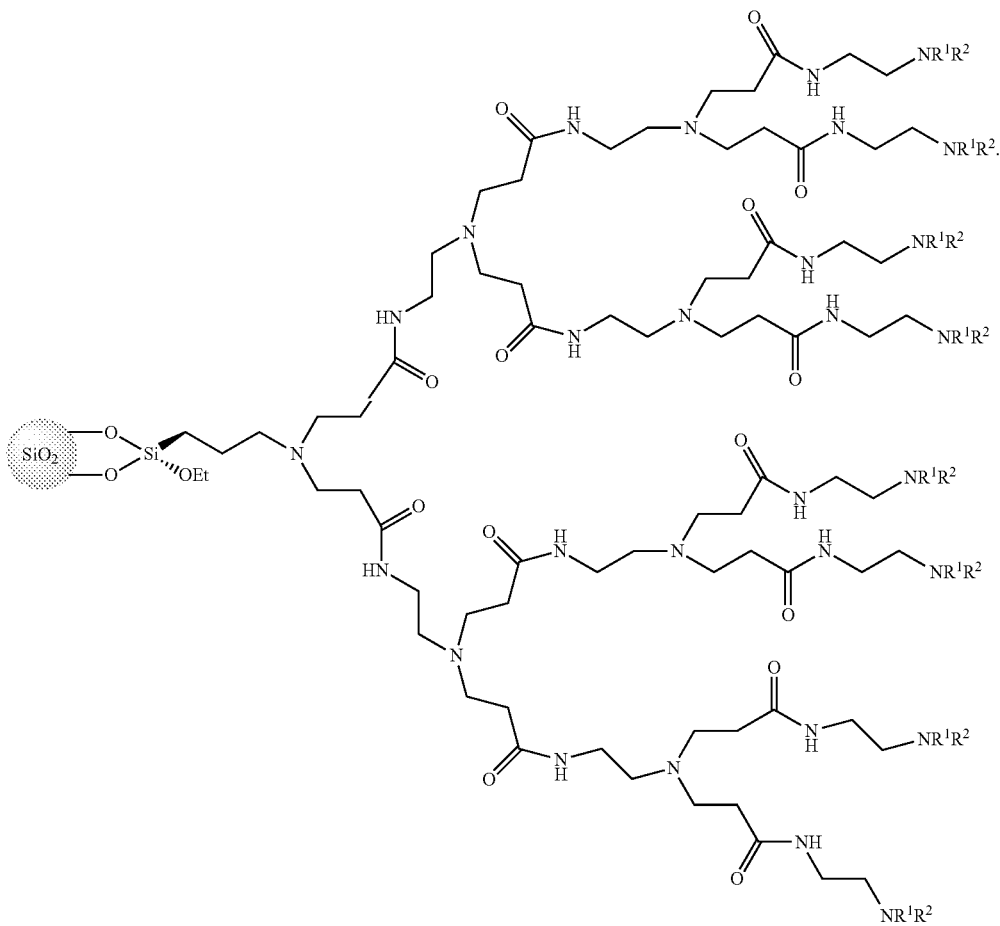

[Formula 3]

In addition, the palladium compound is comprised of conventionally known palladium compounds such as palladium acetate (Pd(OAc)$_2$, here (OAc) is acetoxy group), a palladium salt including palladium chloride (PdCl$_2$), palladium black (Pd), a complex of palladium including tetrakis(triphenylphosphine)palladium (Pd(PPh$_3$)$_4$, here Ph is phenyl group). Among them, the use of palladium acetate is particularly preferable.

Further, the palladium compound is supported on the dendrimer under the condition of being dissolved in an ionic liquid. As for the ionic liquid, it suffice that the ionic liquid can dissolve the palladium compound, and that the ionic liquid is in a state of liquid at a normal temperature, preferably at 35° C. or lower, and there may be used 1-butyl-3-methylimidasolium hexafluorophosphate ([bmim]PF$_6$), 1-hexyl-3-methylimidazolium hexafluorophosphate ([hmim]PF$_6$), 1-butyl-3-methylimidazolium bis(trifluoromethane sulfonyl) imide ([bmim]NTf$_2$) and the like.

A method for producing a bisaryl compound of the invention uses the above mentioned palladium catalyst of the invention, when producing the bisaryl compound by reacting an aromatic halide with an aromatic boronic acid in the presence of the palladium catalyst and a base. Additionally, the aromatic halide and the aromatic boronic acid are not restricted to any specified compounds, and a bisaryl compound can be produced by Suzuki-Miyaura reaction with a combination of any aromatic halide and any aromatic boronic acid.

In the present invention, an organic or an inorganic base can be used as the base without any restriction to the specified base, however, potassium carbonate is particularly preferable. Further, the reaction of an aromatic halide with an aromatic boronic acid proceeds in a conventional organic solvent. The reaction, however, proceeds in a mixture of ethanol and water the most efficiently.

The above mentioned palladium catalyst of the invention has the advantages such as an extremely high turnover number (TON) reaching 100,000, recyclability due to easy recovery by filtration, and an availability in a microreactor. In addition, the method for producing the bisaryl compound using the palladium catalyst requires neither a ligand for the reaction nor an environmental countermeasure, because the reaction proceeds in a mixture of ethanol and water. Furthermore, the reaction proceeds at a room temperature without heating, and a variety of compounds can be utilized for the reaction. Additionally, an ortho-substituted biphenyl compound conventionally difficult for synthesis with a high yield due to the steric barrier can be produced with a high yield. Moreover, the product can be easily isolated without any extraction procedure.

The embodiment of the present invention is described below in details in accordance with the examples. However, the technical scope of the invention is not limited by the examples.

Example 1

Preparation of Palladium Catalyst

1) Preparation of a Dendrimer Comprising a Silica Particle as a Core

The suspension of silica gel (5.0 g, 16 nm of diameter, 200 m²/g of surface area) and gamma-aminotriethoxysilane (in 150 mL of 5% toluene) were refluxed with heating for 8 hours. After the centrifugation, the silica gel was extracted with toluene with a Soxlet's extractor for 24 hours. Then, drying was carried out under reduced pressure at room temperature.

Subsequently, the 0.5 g of the silica gel was added in 20 mL of methanol and 0.2 mL of methylacrylate, and stirred at 50° C. for 24 hours. The silica gel was separated by centrifugation, and washed several times with methanol.

Next, the silica gel was added in 20 mL of methanol and 1.0 mL of ethylenediamine, and stirred at 50° C. for 24 hours. The silica gel was separated by centrifugation, and washed several times with methanol.

Subsequently, the silica gel was added in 20 mL of methanol and 0.4 mL of methylacrylate, and stirred at 50° C. for 24 hours. The silica gel was separated by centrifugation, and washed several times with methanol.

Subsequently, the silica gel was added in 20 mL of methanol and 2.0 mL of ethylenediamine, and stirred at 50° C. for 24 hours. The silica gel was separated by centrifugation, and washed several times with methanol.

Subsequently, the silica gel was added in 20 mL of methanol and 0.4 mL of methylacrylate, and stirred at 50° C. for 24 hours. The silica gel was separated by centrifugation, and washed several times with methanol.

Finally, the silica gel was added in 20 mL of methanol and 2.0 mL of N,N-dimethylethylenediamine, and stirred at 50° C. for 24 hours. The silica gel was separated by centrifugation, washed several times with methanol, and the dendrimer represented in the following formula was obtained.

[Formula 4]

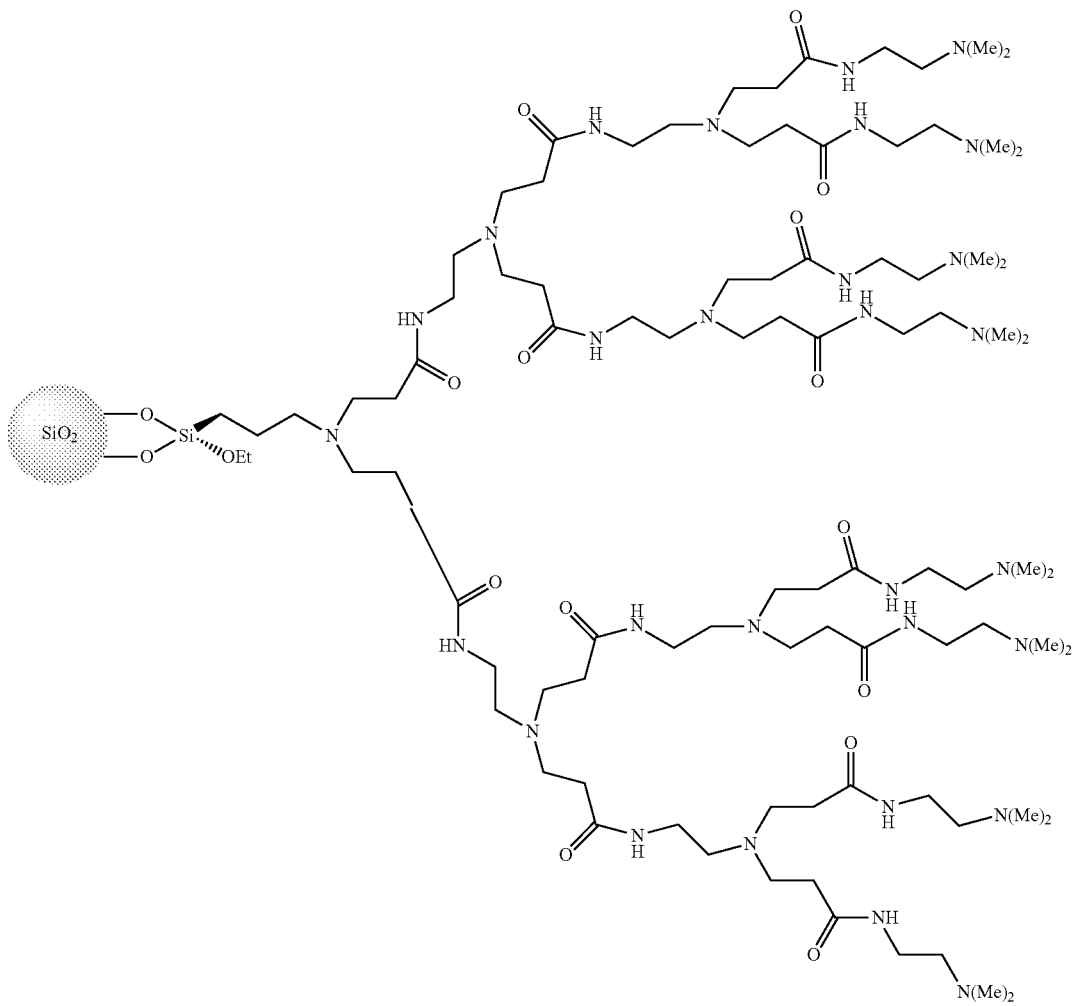

2) Preparation of Palladium Catalyst

A palladium catalyst was prepared by use of 1-butyl-3-methylimidazolium hexafluorophosphate ([bmim]PF$_6$) as an ionic liquid.

The dendrimer (200 mg) prepared by the above methods was placed in a test tube of 10 mL. 1-Butyl-3-methylimidazolium hexafluorophosphate (19 mg, 10% by mass) and palladium acetate (36 mg, 0.16 mmol) dissolved in tetrahydrofuran (2 mL) were added, and stirred at room temperature for 4 hours. THF was removed under reduced pressure, and the surface was rinsed with diethyl ether. Subsequently, the catalyst on the support (247 mg) was obtained after drying under reduced pressure. The loading amount of palladium acetate was 0.65 mmol/g of the support.

Example 2

A bisaryl compound was synthesized as below by use of the palladium catalyst obtained in the example 1.
[Reaction Example 1]
4-Bromoacetophenone (100 mg, 0.50 mmol), phenylboronic acid (85 mg, 0.70 mmol, 1.4 eq.), potassium carbonate (138 mg, 1.0 mmol, 2.0 eq.), the palladium catalyst (8 mg, 0.005 mmol, 0.01 eq.), and 50% aq. ethanol (2.0 mL) were added in a test tube of 10 mL, and stirring at room temperature was started. After stirring for 30 min, the reaction was stopped, and the catalyst was separated with a centrifugal separator, then isolation and purification were carried out by decantation with diethyl ether/ethanol, a short column (ethyl acetate/n-hexane=1/3), and a column (ethyl acetate/n-hexane=1/10), then the intended substance represented in the following formula was obtained (102 mg, 100%).

[Formula 5]

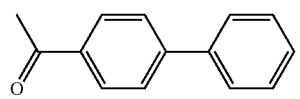

The leakage of palladium into the reaction solution was extremely as low as 2.4 ppm (1%). Further, the used catalyst could be recycled at least 5 times, and the average of the yields was 93%.
[Reaction Example 2]
4-Bromoacetophenone (100 mg, 0.50 mmol), 2-phenylphenylboronic acid (138 mg, 0.70 mmol, 1.4 eq.), potassium carbonate (139 mg, 1.0 mmol, 2.0 eq.), the palladium catalyst (8 mg, 0.005 mmol, 0.01 eq.), and 50% aq. ethanol (2.0 mL) were added in a test tube of 10 mL, and stirring at room temperature was started. After stirring for 30 min, the reaction was stopped, and the catalyst was separated with a centrifuge, then isolation and purification were carried out by decantation with diethyl ether/ethanol, a short column (ethyl acetate/n-hexane=1/3), and a column (ethyl acetate/n-hexane=1/10), then the intended substance represented in the following formula was obtained (134 mg, 98%).

[Formula 6]

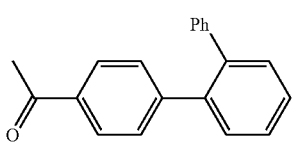

[Reaction Example 3]
4-Bromoacetophenone (101 mg, 0.50 mmol), 4-methoxyphenylboronic acid (106 mg, 0.70 mmol, 1.4 eq.), potassium carbonate (138 mg, 1.0 mmol, 2.0 eq.), the palladium catalyst (8 mg, 0.005 mmol, 0.01 eq.), and 50% aq. ethanol (2.0 mL) were added in a test tube of 10 mL, and stirring at room temperature was started. After stirring for 30 min, the reaction was stopped, and the catalyst was separated with a centrifugal separator, then isolation and purification were carried out by decantation with diethyl ether/ethanol, a short column (ethyl acetate/n-hexane=1/1), and a column (ethyl acetate/n-hexane=1/3), then the intended substance represented in the following formula was obtained (104 mg, 90%).

[Formula 7]

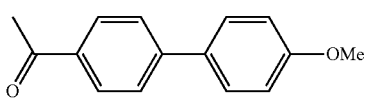

[Other Reaction Examples]
The reactions of various aromatic halides with aromatic boronic acids were carried out using the above mentioned palladium catalyst (0.01 eq.) in 50% aq. ethanol. The results were shown in table 1. The intended substances were obtained with high yields according to a wide variety of substrates.

| | Aromatic halide | Aromatic boronic acid | Product | Temperature (° C.) | Time (h) | Yield (%) |
|---|---|---|---|---|---|---|
| 1 | 1a | 2a | 3a | R.T. | 0.5 | 100 |
| 2 | 1b | 2a | 3a | R.T. | 0.5 | 100 |
| 3 | 1c | 2a | 3a | Reflux | 24 | 14 |

-continued

| | Aromatic halide | Aromatic boronic acid | Product | Temperature (° C.) | Time (h) | Yield (%) |
|---|---|---|---|---|---|---|
| 4 | 1d (4-OTf acetophenone) | 2a | 3a | R.T.-60 | 21 | 47 |
| 5 | 1a (4-bromoacetophenone) | 2b (2-methylphenylboronic acid) | 3b | R.T. | 1 | 98 |
| 6 | 1a | 2c (2-phenylphenylboronic acid) | 3c | R.T. | 10 | 98 |
| 7 | 1a | 2d (4-methoxyphenylboronic acid) | 3d | R.T. | 0.5 | 90 |
| 8 | 1a | 2e (2-methoxyphenylboronic acid) | 3e | R.T. | 4 | 73 |
| 9 | 1a | 2f (2-isopropylphenylboronic acid) | 3f | R.T. | 6 | 95 |
| 10 | 1a | 2g (1-naphthylboronic acid) | 3g | R.T. | 0.5 | 99 |
| 11 | 1e (2-bromotoluene) | 2a | 3h | R.T. | 5 | 62 |

-continued

| | Aromatic halide | Aromatic boronic acid | Product | Temperature (°C.) | Time (h) | Yield (%) |
|---|---|---|---|---|---|---|
| 12 | 1f (OMe, Br-substituted benzene) | 2a | 3i (OMe-biphenyl) | R.T.-60 | 8 | 68 |
| 13 | 1g (1-bromonaphthalene) | 2a | 3j (1-phenylnaphthalene) | R.T. | 4 | 86 |

R.T.: Room Temperature

Example 3

Preparation of Palladium Catalyst

A Palladium catalyst was prepared by use of 1-butyl-3-methylimidazolium bis(trifluoromethane sulfonyl)imide ([bmim]NTf$_2$) as an ionic liquid.

The dendrimer (50 mg) prepared by the methods described in the example 1 was placed in a test tube of 10 mL. 1-Butyl-3-methylimidazolium bis(trifluoromethylsulfonyl)imide (13 mg, 26% by mass) and palladium acetate (15 mg, 0.06 mmol) in tetrahydrofuran (4 mL) were added, and stirred at room temperature for 4 hours. THF was removed under reduced pressure, and the surface was rinsed by diethyl ether. Then, after drying under reduced pressure, the catalyst on the support (60 mg) was obtained. The loading amount of palladium acetate was 0.83 mmol/g of the support.

Example 4

Reaction Example

A bisaryl compound was synthesized by using the palladium catalyst obtained in example 3.

4-Bromoacetophenone (100 mg, 0.50 mmol), phenylboronic acid (85 mg, 0.70 mmol, 1.4 eq.), potassium carbonate (138 mg, 1.0 mmol, 2.0 eq.), the palladium catalyst (6 mg, 0.005 mmol, 0.01 eq.), and 50% aq. ethanol (2.0 mL) were added in a test tube of 10 mL, and stirring at room temperature was started. After stirring for 45 min, the reaction was stopped, and the catalyst was separated with a centrifugal separator, then isolation and purification were carried out by decantation with diethyl ether/ethanol, a short column (ethyl acetate/n-hexane=1/3), and a column (ethyl acetate/n-hexane=1/10), then the intended substance represented in the following formula was obtained (100 mg, 100%).

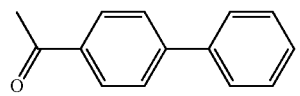

[Formula 8]

Example 5

Preparation of Palladium Catalyst

A Palladium catalyst was prepared by use of 1-hexyl-3-methylimidazolium hexafluorophosphate ([hmim]PF$_6$) as an ionic liquid.

The dendrimer (50 mg) prepared by the method described in the example 1 was placed in a test tube of 10 mL. 1-Butyl-3-hexylimidazolium hexafluorophosphate (21 mg, 30% by mass) and palladium acetate (15 mg, 0.06 mmol) in tetrahydrofuran (4 mL) were added, and stirred at room temperature for 4 hours. THF was removed under reduced pressure, and the surface was rinsed by diethyl ether. Subsequently, after drying under reduced pressure, the catalyst on the support (75 mg) was obtained. The loading amount of palladium acetate was 0.84 mmol/g of the support.

Example 6

Reaction Example

A bisaryl compound was synthesized by using the palladium catalyst obtained in example 5.

4-Bromoacetophenone (100 mg, 0.50 mmol), phenylboronic acid (85 mg, 0.70 mmol, 1.4 eq.), potassium carbonate (138 mg, 1.0 mmol, 2.0 eq.), the palladium catalyst (6 mg, 0.005 mmol, 0.01 eq.), and 50% aq. ethanol (2.0 mL) were added in a test tube of 10 mL, and stirring at room temperature was started. After stirring for 15 min, the reaction was stopped, and the catalyst was separated with a centrifugal separator, then isolation and purification were carried out by decantation with diethyl ether/ethanol, a short column (ethyl acetate/n-hexane=1/3), and a column (ethyl acetate/n-hexane=1/10), then the intended substance represented in the following formula was obtained (100 mg, 100%).

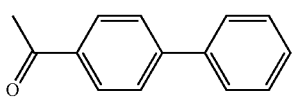

[Formula 9]

Comparative Example 1

A palladium catalyst supported on the dendrimer was prepared without using ionic liquid, then the reaction using the catalyst was examined.

Under nitrogen atmosphere, the dendrimer (99.9 mg) prepared by the methods described in the example 1 was added in a test tube of 10 mL. Subsequently, palladium acetate (22.4 mg, 0.10 mmol) was dissolved in tetrahydrofuran (1.5 mL), the solvent was added dropwise through a cannula, and stirred at room temperature for 4 hours. After stirring, the solvent was removed under reduced pressure, and the reaction mixture was washed with diethyl ether, then dried under reduced pressure. The catalyst on the support (106.3 mg) was obtained and the loading amount of palladium acetate was 0.94 mmol/g of the support.

4-Bromoacetophenone (100.0 mg, 0.50 mmol), phenylboronic acid (85.4 mg, 0.70 mmol, 1.4 eq.), potassium carbonate (139.8 mg, 1.0 mmol, 2.0 eq.), the palladium catalyst (26.9 mg, 0.025 mmol, 0.05 eq.), and 50% aq. ethanol (2.0 mL) were added in a test tube of 10 mL, and stirring at room temperature was started. After stirring for 24 hours, the reaction was stopped, then isolation and purification were carried out by decantation with diethyl ether/ethanol, a short column (ethyl acetate/n-hexane=1/7), and a column (ethyl acetate/n-hexane=1/7), then the mixture of the intended substance and the unreacted materials were obtained (79.8 mg). From the measurement of integration values of $^1$H-NMR (270 MHz), the intended substance and the unreacted raw materials were calculated as 49.6 mg (50.6%) and 30.2 mg (30.3%), respectively.

As mentioned above, the activity of the palladium catalyst supported on the dendrimer without use of an ionic liquid was low, and in the reaction of 4-bromoacetophenone with phenylboronic acid in 50% ethanol at room temperature for 24 hours, the yield was 51%.

Comparative Example 2

A catalyst was prepared without use of the dendrimer, and the reaction by use of the catalyst was examined.

Palladium acetate was immobilized by use of 1-butyl-3-methylimidazolium hexafluorophosphate on amorphous alumina having the surface modified by diethylaminopropyl group. By using the catalyst, the reaction of 4-bromoacetophenone with 2-methylphenylboronic acid in 50% aq. ethanol was carried out by reflux with heating for 8 hours. However, all of the unreacted raw materials were completely recovered. Further, the unreacted raw materials were also recovered completely in the reaction of 4-bromoacetophenone with 2,6-dimethylphenylboronic acid.

As mentioned above, in the case of preparation of the catalyst without the dendrimer, the reaction did not proceed entirely.

The invention claimed is:

1. A method for producing a bisaryl compound, using a palladium catalyst when producing the bisaryl compound by reacting an aromatic halide with an aromatic boronic acid in the presence of the palladium catalyst and a base, wherein the palladium catalyst comprises a palladium compound dissolved in an ionic liquid and supported on a dendrimer containing a silica particle as a core, wherein the dendrimer is represented in the following formula, wherein $R^1$, $R^2$ is selected from hydrogen and methyl group

[Formula 1]

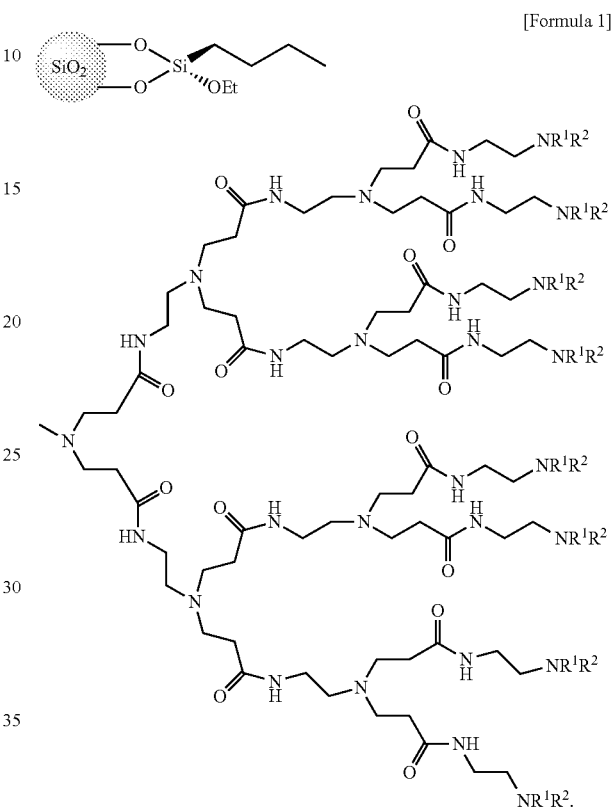

2. The method for producing the bisaryl compound of claim 1, wherein a diameter of the silica particle is in a range of 1 to 100 nm.

3. The method for producing the bisaryl compound of claim 1, wherein the palladium catalyst is palladium acetate.

4. The method for producing the bisaryl compound of claim 3, wherein the ionic liquid is 1-butyl-3-methylimidazolium hexafluorophosphate.

5. The method for producing the bisaryl compound of claim 3, wherein the ionic liquid is 1-butyl-3-methylimidazolium bis(trifluoromethane sulfonyl)imide.

6. The method for producing the bisaryl compound of claim 3, wherein the ionic liquid is 1-hexyl-3-methylimidazolium hexafluorophosphate.

7. The method for producing the bisaryl compound of claim 1, wherein the base is potassium carbonate and the aromatic halide reacts with the aromatic boronic acid in a mixture solvent of water and ethanol.

* * * * *